(12) United States Patent
Sakuta

(10) Patent No.: US 6,930,220 B2
(45) Date of Patent: Aug. 16, 2005

(54) ADHERING THERAPEUTIC TOOL

(76) Inventor: Masayuki Sakuta, 207, 4-11-9, Kamiaoki, Kawaguchi-shi, Saitama-ken (JP)

( * ) Notice: Subject to any disclaimer, the term of this patent is extended or adjusted under 35 U.S.C. 154(b) by 466 days.

(21) Appl. No.: 09/947,558

(22) Filed: Sep. 7, 2001

(65) Prior Publication Data
US 2002/0099322 A1 Jul. 25, 2002

(30) Foreign Application Priority Data
Jan. 24, 2001 (JP) .................................... 2001-015781

(51) Int. Cl.$^7$ .................................................. A61F 13/00
(52) U.S. Cl. .......................... 602/41; 602/48; 600/15; 601/15
(58) Field of Search ................................ 609/304–308; 602/41–59, 60, 67, 74, 75, 2; 600/15; 601/15

(56) References Cited

U.S. PATENT DOCUMENTS

| 4,489,711 A | * | 12/1984 | Latzke | .................. | 600/15 |
| 6,506,403 B1 | * | 1/2003 | Yu | .................. | 424/443 |

FOREIGN PATENT DOCUMENTS

EP   315732 A1 * 5/1989 ........... A61F/13/02

* cited by examiner

Primary Examiner—Kim M. Lewis
(74) Attorney, Agent, or Firm—Birch, Stewart, Kolasch & Birch, LLP

(57) ABSTRACT

There is disclosed an adhering therapeutic tool in which a polymer granular matter including a metallic solid material (1) composed of powder of pure gold, etc. and an ore material (2) containing 75% or more of a quartz component is fixed to a central part of a viscous sheet (3) with the former located outside and the latter located inside.

6 Claims, 1 Drawing Sheet

ADHERING THERAPEUTIC TOOL

BACKGROUND OF THE INVENTION

1. Field of the Invention

This invention relates to an adhering therapeutic tool, and more particularly to a tool to be adhered to an effective spot for therapeutic treatment.

2. Related Art

It is already made clear that a living body of the human being is created such that all commands from the brain to various muscles are functioned by electrical signal. It is because of the interruption of the electrical signal that paralysis of the motor nerve occurs due to traffic accidents and surgical treatment. Even if the degree of adverse effect to the living body is not so serious as to cause paralysis of the motor nerve, degraded function may often cause numbness, lack of sensitivity, trembling, coldness and the like.

Various proposals have been made as a method for recovering the degraded function. The proposals include acupuncture, moxibustion, finger pressure therapy, massage, magnetic treatment, feeding of electricity, feeding of low frequency and so on. Although those therapeutic treatments have been widely accepted, they are not yet completely satisfactory in effect.

The present invention has been accomplished in view of the above.

SUMMARY OF THE INVENTION

It is, therefore, an object of the present invention to provide an adhering therapeutic tool which adopts entirely different principles from those of the conventional devices and in which in order to prevent the occurrence of paralysis of the motor nerve of the human being, effective acupuncture spots are stimulated to maintain an electrical well-balance of the human body.

To achieve the above object, the feature of the present invention resides in an adhering therapeutic tool in which a polymer granular matter including a metallic solid material composed of powder of pure gold, etc. and an ore material containing 75% or more of a quartz component is fixed to a central part of a viscous sheet with the former located outside and the latter located inside.

The polymer granular matter may be provided with a magnetic member.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE EMBODIMENT

Figure 1:
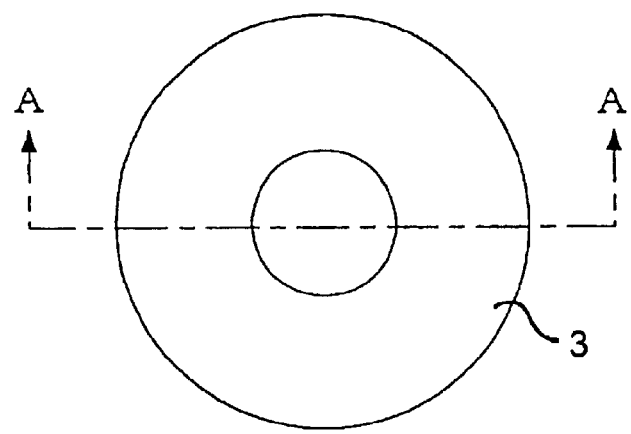
FIG. 1 is an enlarged front view showing an overall picture of an adhering therapeutic tool according to one embodiment of the present invention.
Figure 2:
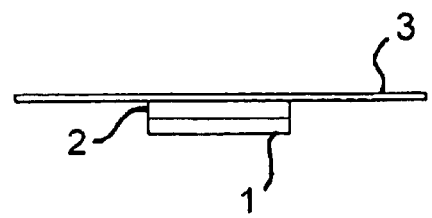
FIG. 2 is an enlarged side view of the above.

One embodiment of the present invention will now be described with reference to the accompanying drawings.

Reference numeral 1 denotes a metallic solid material composed of powder of pure gold or gold alloy. The pure gold composing the metallic solid material is a materially highly stabilized best conductor as a metal. Reference numeral 2 denotes an ore material composed of powder of a natural mineral which is chiefly composed of a quartz. The ore material is a silicate mineral called quartz porphyry which contains 75% or more of a quartz as a chief component. The remaining components include 7% or more of aluminum oxide and others such as iron oxide, potassium oxide, titanium oxide, etc. The ore material 2 may be mixed with a proper amount of a magnetic powder.

The metallic solid material 1 such as pure gold powder is polymerized on an upper surface of the ore material 2 so as to form a layer. Such a layer structure formed by the two materials 1 and 2 is not limited to two layers. It may be of a multilayer of three or more layers. In the case where the magnetic member is employed, it may be disposed at an intermediate location between the metallic solid material 1 and the ore material 2.

The polymer granular matter composed of the two materials 1 and 2 is set to 2 mm or less in diameter. This range of a diameter is important for the following reason. An energy (far infrared radiation, minus ion and line of magnetic force) imparted to matter which the ore material has and an electric potential are fed to the human body and as a result, it serves as a spot having a function. The spot of the polymer granular matter composed of the two materials 1 and 2 contacts the effective acupuncture spot of the human body.

Pure gold, etc. is the best conductors and generates a small amount of electricity in the multi-structure formed of the metal and the ore. As a consequence, the circulatory function of the body liquid can be improved.

Reference numeral 3 denotes a viscous sheet. The polymer granular matter is fixed to a central part of the viscous surface of the sheet 3 with the metallic solid material 1 located outside and the ore material 2 located inside.

The viscous sheet 3 is set to 10 mm or less in diameter. The configuration of the viscous sheet 3 is optional. Namely, it may be selected from, for example, circle, square, star, hart and the like. By properly selecting any one of them, there can be provided a fashionability as mentioned above.

Figure 3:
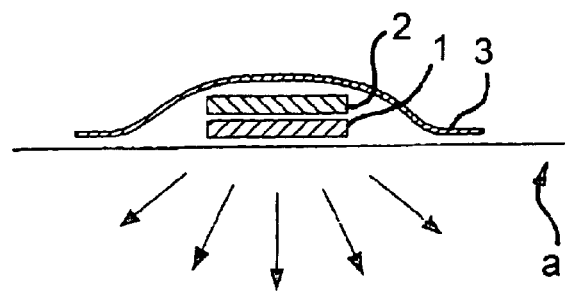
FIG. 3 is an explanatory view showing how energy, etc. is transmitted when the tool is adhered to an effective acupuncture spot on the human body.

In FIG. 3, reference character a refers to a skin of the human body.

The effect of the invention will now be described. When the viscous sheet according to the present invention is adhered to the effective acupuncture spot of the human body, the heat function of the far infrared radiation generated by the ore material composing the polymer granular matter located at a central part of the sheet, the energy of the minus ion and the line of magnetic force of the magnetic member can be transmitted directly to the effective acupuncture spot of the human body through the metallic solid material of a good conductor such as a pure gold.

Since the pure gold, etc. is the best conductor, the very small electricity generated in the multi-structure formed of the metal and the ore corrects the torsion of the electric well-balance of the human body and reduces the size of the molecular structure of a body liquid. As a consequence, the circulating function of the body liquid in the human body can be improved and the life energy can be enhanced.

Obviously, many modifications and variations of the present invention are possible in light of the above teachings. It is, therefore, to be understood that within the scope of the appended claims, the invention may be practiced otherwise than as specifically described.

What is claimed is:

1. An adhering therapeutic tool comprising a polymer granular matter including a metallic solid material composed of powder of pure gold and an ore material containing 75% or more of a quartz compound is fixed to a central part of a viscous sheet with the former located outside and the latter located inside.

2. The adhering therapeutic tool according to claim 1, wherein said metallic solid material and said ore material composing said polymer granular matter is set to 2 mm or less in diameter.

3. The adhering therapeutic tool according to claim 1 or 2, wherein said polymer granular matter is optional in configuration and color.

4. The adhering therapeutic tool according to claim 1 or 2, wherein said viscous sheet is optional in configuration and color.

5. The adhering therapeutic tool according to claim 1, wherein said ore material composing said polymer granular matter is mixed with a magnetic powder.

6. The adhering therapeutic tool according to claim 1, wherein a magnetic layer is disposed between said metallic solid material and said ore material composing said polymer granular matter.

* * * * *